United States Patent [19]

Riff

[11] Patent Number: 5,040,536
[45] Date of Patent: Aug. 20, 1991

[54] INTRAVASCULAR PRESSURE POSTURE DETECTOR

[75] Inventor: Kenneth M. Riff, Plymouth, Minn.

[73] Assignee: Medtronic, Inc., Minneapolis, Minn.

[21] Appl. No.: 473,265

[22] Filed: Jan. 31, 1990

[51] Int. Cl.5 ............................ A61B 5/02; A61N 1/36
[52] U.S. Cl. ............................ 128/419 PG; 128/672;
                                       128/675; 128/748; 604/66; 600/17
[58] Field of Search ............... 128/672, 673, 675, 748,
                                       128/419 PG; 604/66; 600/17

[56] References Cited
U.S. PATENT DOCUMENTS

| 4,052,991 | 10/1977 | Zacouto | 128/419 PG |
| 4,566,456 | 1/1986 | Koning et al. | 128/675 |
| 4,777,951 | 10/1988 | Cribier et al. | 128/748 |
| 4,802,481 | 2/1989 | Schroeppel | 128/419 PG |
| 4,886,064 | 12/1989 | Strandberg | 128/419 PG |
| 4,932,408 | 6/1990 | Schaldach | 128/419 PG |

Primary Examiner—Lee S. Cohen
Assistant Examiner—K. M. Pfaffle

[57] ABSTRACT

Apparatus and method for detecting changes in the posture of a patient. Two pressure sensors are chronically implanted at different places in the cardiovascular system. One may be positioned in the right heart, for example, and the other placed in the inferior vena cava. The positioning is selected for ease of chronic implantation. However, the positions chosen must be such that the differences in pressure with changes in posture are differentially measurable. The differences in pressure changes sensed at the two positions enable electronic circuitry to determine changes in posture of the patient. These changes in posture may be used to indicate associated physiological changes such as increased or decreased demand on the cardiovascular system or changes in other homeostatic functions. Compensation for this changing cardiovascular or other homeostatic functions may be partially met through increasing or decreasing the escape interval of a demand cardiac pacemaker or by altering the drug delivery regimen of an implantable drug dispenser.

7 Claims, 6 Drawing Sheets

INTRAVASCULAR PRESSURE POSTURE DETECTOR

BACKGROUND OF THE INVENTION

1. Field of the Invention

The present invention generally relates to implantable medical devices, and more specifically, relates to chronically implantable devices for determination of the posture of a patient.

2. Description of the Prior Art

Posture detection devices have been known in the art for some time. Often these are implanted and used for control of the pacing rate of an artificial cardiac pacer. The typical method is through the use of gravity using a mercury switch, for example. The gravity switch method, of course, provides only a binary or two state output. Either the switch is open or it is closed.

Intravascular pressure sensors are also known in the art. U.S. Pat. No. 4,407,296 issued to Anderson teaches a chronically implantable pressure transducer suitable for use in the cardiovascular system. A pressure transducer with an improved electronic circuit is taught in U.S. Pat. No. 4,432,372, issued to Monroe. A further improved pressure transducer is taught in U.S. Pat. No. 4,485,813, issued to Anderson, et al. These pressure sensors have been directed to the control of artificial cardiac pacers using algorithms which convert measurements of pressure or change of pressure into pacing rate.

U.S. Reissue Pat. No. 30,372, issued to Mirowski, et al. teaches control of an implantable defibrillator using an intravascular pressure sensor. None of these references teaches the use of differential pressure measurement to determine the posture of the patient.

SUMMARY OF THE INVENTION

The present invention uses at least two pressure sensors which are chronically implanted in the vascular system. These sensors are positioned such that changes in pressure are sensed in response to changes in posture of the patient. To determine the posture of the patient, the sensors are placed to sense differential changes in pressure with changes in posture.

This differential pressure change results from gravitational effects upon different points within the vascular system. For example, with pressure sensors in the right heart and the inferior vena cava of a supine patient, the pressure measurements are approximately the same. However, when the patient is erect, the sensor in the inferior vena cava will measure a greater pressure than the sensor in the right heart. It is this pressure differential which identifies the patient as erect.

Because the sensors measure the actual pressure, the differential pressure changes continuously from completely supine to completely erect. Therefore, a patient's differential pressure measurement when sitting up can be distinguished from measurements taken when either supine or erect. Other posture variations can be detected as well.

A further advantage of determining posture with differential pressure is that factors which result in equal pressure changes to all of the sensors are cancelled out and thereby eliminated. Typical of these factors are differences in altitude and atmospheric pressure. Also eliminated in this way are transients such as experienced in coughing or sneezing.

The posture measurement may be used in a number of ways. A typical application is in cardiac pacing. By assuming that an upright patient has a higher cardiac demand than a supine patient, the posture determination is readily used to increase pacing rate for patients in the upright posture. Alternatively, the posture determination may be used to vary the drug delivery regimen of an implanted drug dispenser, for example, by increasing or initiating the dispensing of a cardiac or other drug. Generally, the invention may be useful in conjunction with any implantable device which provides a therapeutic treatment to the body, for varying the treatment in response to postural changes.

BRIEF DESCRIPTION OF THE DRAWINGS

Additional objects and features of the present invention will be more apparent as the same becomes further understood from the following description in which the preferred embodiments are set forth in detail in conjunction with the accompanying drawings and in which like reference numerals refer to like parts and wherein.

DETAILED DESCRIPTION OF THE PREFERRED EMBODIMENTS

The present invention utilizes at least two chronically implantable pressure sensors positioned within the cardiovascular system. In the preferred mode, two pressure sensors are used, however, additional sensors may be employed in accordance with the teaching of the present invention. The pressure sensor taught in U.S. Pat. No. 4,485,813 issued to Anderson, et al. and incorporated herein by reference is the sensor preferred for this application. Other suitable sensors are taught in U.S. Pat. No. 4,432,372 issued to Monroe and U.S. Pat. No. 4,407,296 issued to Anderson, both of which are herein incorporated by reference.

Figure 1:
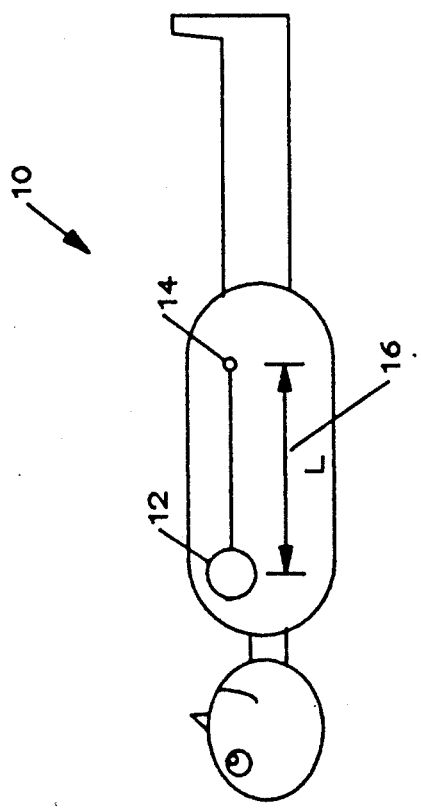
FIG. 1 is a schematic diagram showing placement of two pressure sensors in a patient in a supine position.

FIG. 1 is a schematic view of a patient 10 in a supine position. The patient 10 has two pressure sensors such as discussed above chronically implanted in the cardiovascular system. The first of these sensors is implanted in the right side of heart 12 using normal implant techniques. The second pressure sensor is implanted in the inferior vena cava at position 14. A linear distance 16 of L units separates the two pressure sensors. If the patient 10 is lying horizontally, the pressure sensed within heart 12 and in the inferior vena cava by the pressure sensor at position 14 will be approximately the same.

Figure 2:
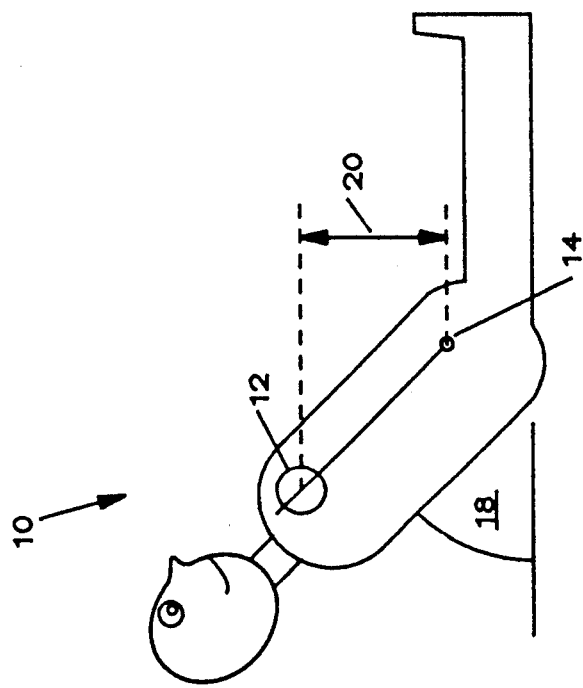
FIG. 2 is a schematic diagram showing placement of two pressure sensors in a patient in a partially seated position.

FIG. 2 is a schematic view of patient 10 having the same chronically implanted pressure sensors. In this view, however, patient 10 is in a partially seated position. As can be seen in the drawing, the torso of patient 10 is inclined at an angle 18 from the horizontal. This causes the pressure sensor in heart 12 to be higher than the pressure sensor at position 14. The distance in elevation may be computed from the distance L between the sensor (see also FIG. 1) and the angle 18 of inclination of the torso. 18. The difference in elevation 20 is L times the sine of angle.

Using standard hydraulic principles, one can readily see that the pressure sensed within heart 12 will be less than that measured by the pressure sensor at position 14 by an amount proportional to elevation 20. By measuring this pressure differential, the angle 18 can thus be estimated. In this way the degree to which the torso of patient 10 is erect can be estimated.

Notice that in this embodiment the pressure differential of a fully seated patient 10 and a standing patient 10 cannot be distinguished. If it were necessary to make such a determination, the pressure sensor at position 14 must be moved below the torso into one of the legs. To do so, however, complicates the implant procedure, and so should be done only if that degree of precision is required for the application.

Figure 3:
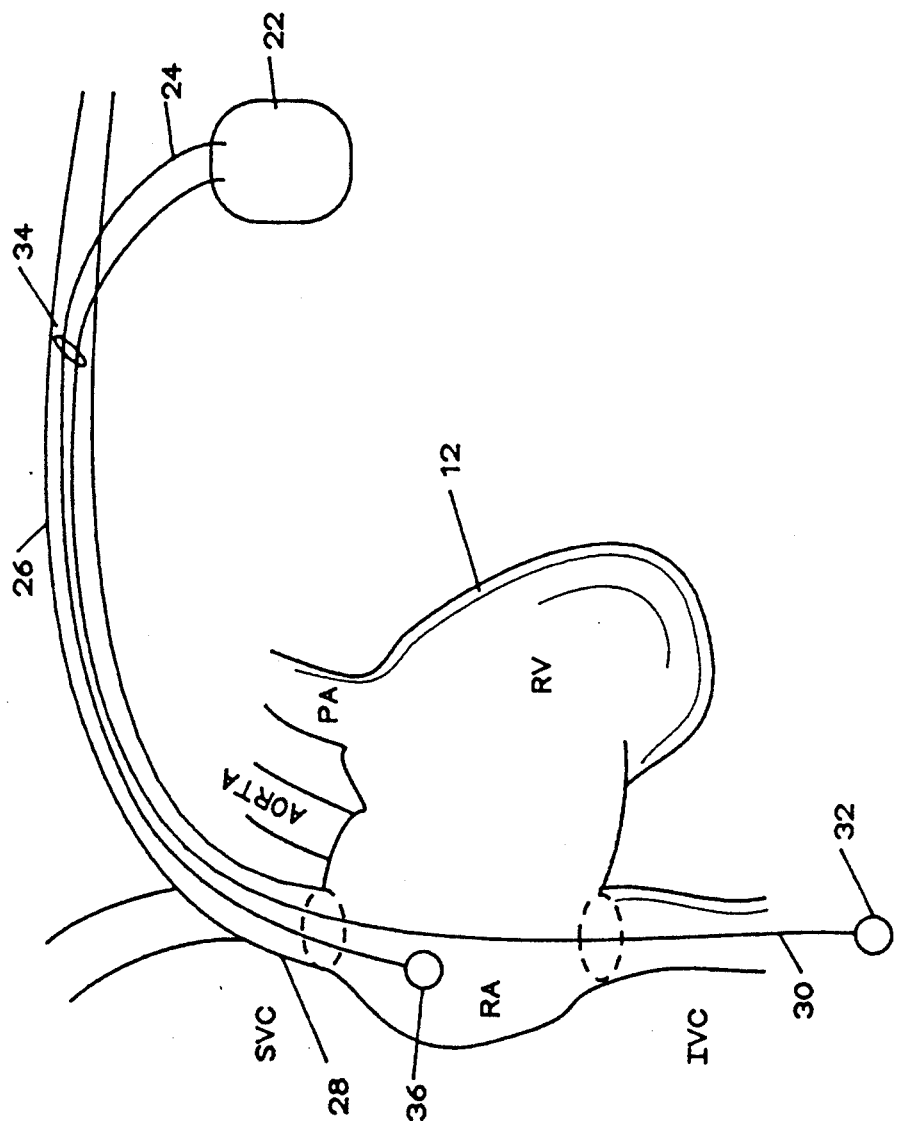
FIG. 3 is a schematic diagram showing preferred placement of two pressure sensors in the vascular system of a patient.

FIG. 3 is a schematic diagram of the two pressure sensors as implanted in the Cardiovascular system. Heart 22 has pressure sensor 36 implanted within the right atrium as shown. It is coupled via electrical lead 24 through the venous system to implantable pulse generator in the same fashion as with transvenous cardiac pacing applications.

Similarly pressure sensor 32 is positioned in the inferior vena cava (see also FIGS. 1 and 2). Pressure sensor 32 is electrically coupled to implantable pulse generator 22 via transvenous lead 30. Both leads 24 and 30 proceed through the subclavian vein 26 from implantable pulse generator 22 after entry at point 34. Entry to the right atrium of heart 12 is via superior vena cava 28.

In the preferred embodiment, implantable pulse generator 22 functions as an artificial cardiac pacer. The necessary pacing lead is not shown for clarity. However, this application is to be understood as typical and not limiting of the scope of the present invention.

In the illustrated embodiment, the pressure sensors are located on two separate leads. However, in some cases, it may be desirable to locate both pressure sensors on the same lead. Differential pressure sensing using a single pressure transducer as illustrated in the above cited U.S. Pat. No. 4,407,296 rather than two separate pressure sensors may also be desirable in some circumstances.

Figure 4:
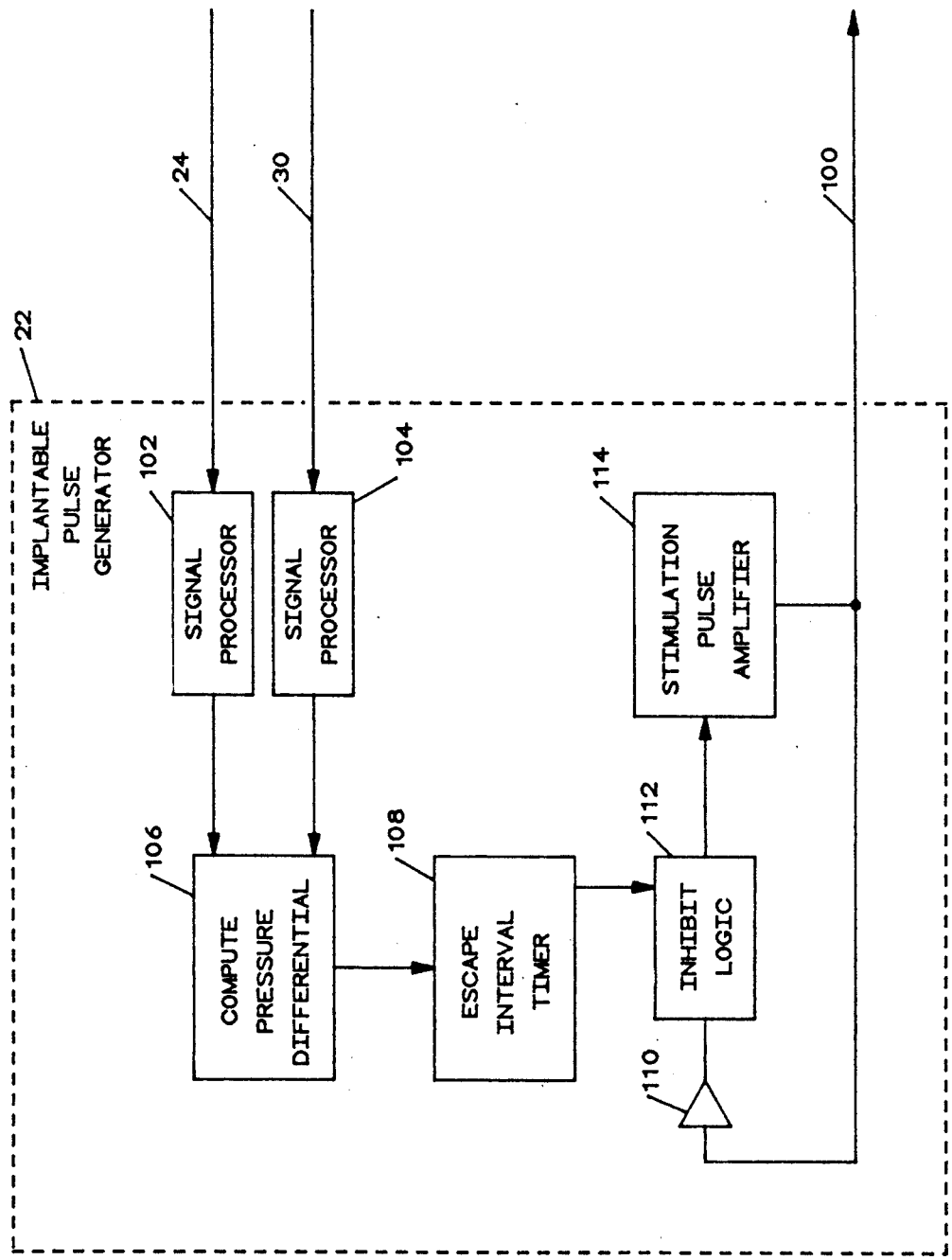
FIG. 4 is a block diagram of an implantable pulse generator incorporating circuitry to vary artificial pacing rate with posture changes determined by differential pressure measurement.

FIG. 4 is a block diagram of implantable pulse generator 22. Leads 24 and 30 are shown as transferring the signals from pressure sensors 36 and 32, respectively. Signal processors 102 and 104 amplify and integrate these signals. The difference in pressure experienced by the two pressure sensors is determined by computed pressure differential circuitry 106. This circuitry controls the escape interval timer 108 using standard voltage control oscillator circuitry. The greater the pressure differential, the shorter the interval produced by escape interval timer 108.

FIG. 4 is intended to be exemplary of the general type of circuitry to be employed in the present invention. However, alternate circuitry may also be employed. For example, signal processors 102, 104 may function as low pass filters, or integration/filtering may be performed after computation of the pressure differential, as in an embodiment employing a single, differential pressure transducer.

Sense amplifier 110, inhibit logic 112, and stimulation pulse amplifier 114 operate as in a normal demand pacemaker. Sensing and stimulation is provided using a standard transvenous pacing lead 100. The pacing output of implantable pulse generator 22 differs from the normal demand pacer only that the underlying artificial pacing rate is decreased as the pressures sensed by the two pressure sensors (i.e. pressure sensors 32 and 36) are more nearly the same and increased as the pressure differential is increased.

Figure 5:
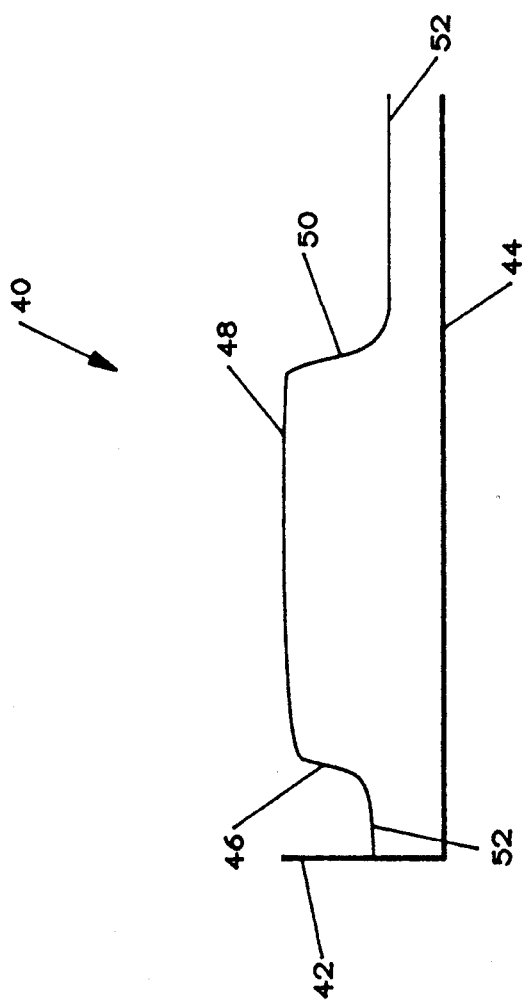
FIG. 5 is a graphic representation of the pressure measured by a single sensor in a patient changing posture; and, FIG. 6 is a graphical representation of the pressure measurements taken from two sensors and the resulting differential.

FIG. 5 is a graphical representation 40 of the idealized output of pressure sensor 32 with changes in patient posture. The projection along axis 42 is the pressure sensed (and hence voltage output of the pressure sensor). The projection along axis 44 is the time over which a number of posture changes take place. The level at 52 shows the measurement when the patient is supine. The patient sits up at 46 resulting in level 48. The patient lies down again at 50 resulting in supine level 52. Notice with this idealized data that posture changes could be monitored with a single pressure sensor.

Figure 6:
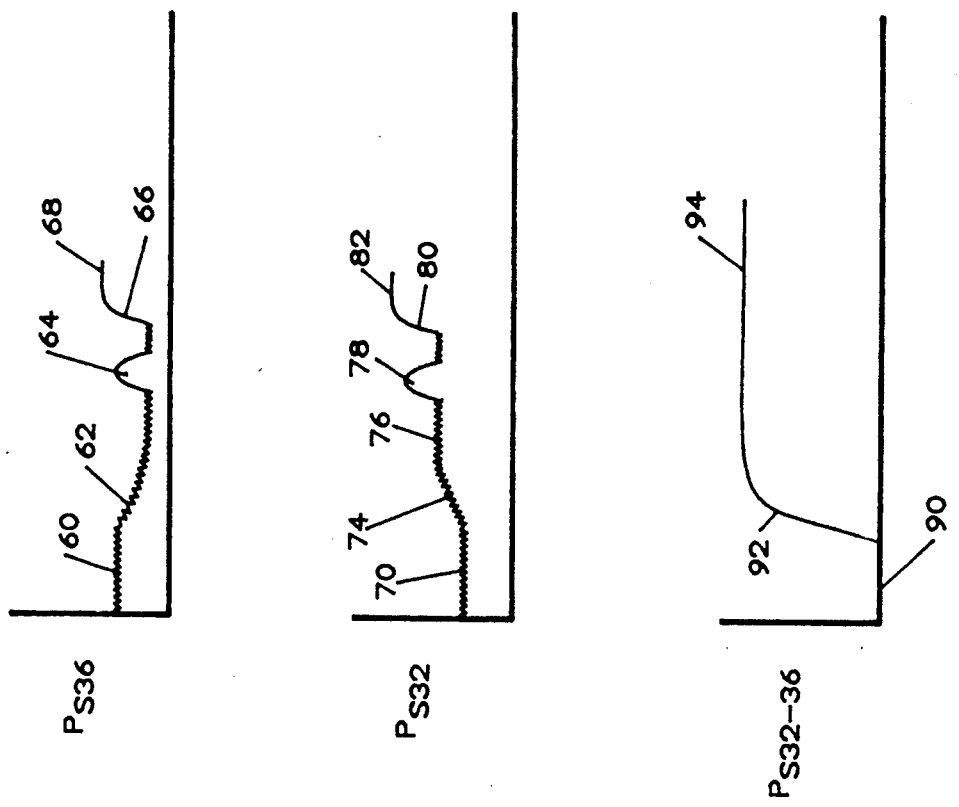

FIG. 6 is a graphical representation of the outputs of both pressure sensors and the computed pressure differential along the same time axis showing some typical transient conditions.

The upper chart shows the pressure level 60 measured by pressure sensor 36 while patient 10 is supine. As the patient rises, the pressure measured by pressure sensor 36 actually decreases to level 62. The pressure increases at 64 and 66 are not related to posture changes. The increase at 64 is a short term transient such as a sneeze or cough. The change beginning at 66 and resulting in level 68 is of longer duration. It may be of physiological causes such as elevated central venous blood pressure or external causes such as change in altitude (e.g. as in an airplane or elevator). In either situation, the non-posture change is detected as a pressure change by pressure sensor 36.

The middle graph shows the output of pressure sensor 32 over the same time period. Notice that the supine level is 70. As the patient 10 rises, it is detected as pressure increase 74 resulting in level 76. Transient pressure rise 78 and non-posture change pressure rise 80 resulting in new pressure level 82 are detected as with pressure sensor 36.

The bottom graph shows the pressure differential of the two pressure sensors. It corresponds to the output of computed pressure differential 106 (see also FIG. 4). Level 90 shows essentially no pressure differential. It corresponds to the time when patient 10 is in the supine position. In the preferred embodiment this results in the longest escape interval (or the lowest underlying pacing rate). As the patient rises, the pressure differential is increased at 92 resulting in new level 94. This corresponds to a shorter escape interval.

Notice that the pressure differential curve does not contain transient 64/78 nor non-posture pressure change 66/80. This is because the differential remains the same when both sensors are subjected to the same non-posture pressure changes.

Other applications of the present invention are readily apparent to those in the art without deviation from the scope of the claims hereto attached.

I claim:

1. A cardiac pacemaker including means for generating stimulus pulses at a pacing rate, wherein the improvement comprises:
   means for measuring a pressure differential between two differing points within the cardiovascular system of a patient such that one of said points is above the other of said points when said patient is in an upright posture; and
   means responsive to the measurement of said pressure differential for varying said pacing rate.

2. A device according to claim 1 wherein said means for measuring said pressure differential comprises first and second pressure sensors each adapted to be located adjacent one of said two differing points.

3. A medical electrical stimulator, comprising:
   pulse generator means for generating stimulus pulses for application to a patient's body at a predetermined rate;
   means for measuring a pressure differential between first and second locations within the cardiovascular system of a patient, said first location above said second location when said patient is in an upright posture; and
   means responsive to the measurement of said pressure differential for varying said predetermined rate.

4. A stimulator according to claim 3, wherein said pulse generator comprises means for delivering cardiac pacing pulses to the heart of said patient.

5. A stimulator according to claim 4 further comprising electrical lead means on which said pressure differential measuring means is located, said electrical lead means coupling said pressure differential measuring means to said varying means.

6. A stimulator according to claim 5 wherein said electrical lead means comprises first and second electrical leads and wherein said pressure differential measuring means comprises first and second pressure sensors, each of said pressure sensors mounted on a different one of said first and second electrical leads.

7. A stimulator according to claim 5 wherein said means for measuring a pressure differential comprises a single pressure sensor mounted to said electrical lead means.

* * * * *